United States Patent [19]

Murphy et al.

[11] Patent Number: 4,983,377
[45] Date of Patent: Jan. 8, 1991

[54] SILICONE HAIRSPRAY COMPOSITIONS

[75] Inventors: Carolyn S. Murphy, Mason, Ohio; Mark R. Prausnitz, Somerville, Mass.

[73] Assignee: The Procter & Gamble Company, Cincinnati, Ohio

[21] Appl. No.: 429,894

[22] Filed: Oct. 31, 1989

[51] Int. Cl.$^5$ ............................................. A61K 7/00
[52] U.S. Cl. ........................................ 424/47; 424/70; 424/71
[58] Field of Search ............................... 424/47, 70, 71

[56] References Cited

U.S. PATENT DOCUMENTS

| | | | |
|---|---|---|---|
| 2,643,375 | 6/1953 | Gant | 132/7 |
| 3,325,439 | 6/1967 | Steinbach | 260/32.8 |
| 3,681,122 | 8/1972 | Demicone et al. | 117/124 |
| 3,928,558 | 12/1975 | Cheesman et al. | 424/47 |
| 3,957,970 | 5/1976 | Korkis | 424/70 |
| 3,964,500 | 6/1976 | Drakoff | 132/7 |
| 4,152,416 | 5/1979 | Spitzer et al. | 424/46 |
| 4,174,386 | 11/1979 | Spitzer et al. | 424/47 |
| 4,185,087 | 1/1980 | Morlino | 424/70 |
| 4,221,688 | 9/1980 | Johnson et al. | 260/29.2 |
| 4,235,873 | 11/1980 | Packman | 424/47 |
| 4,344,763 | 8/1982 | Tolgyesi et al. | 8/127.51 |
| 4,364,837 | 12/1982 | Pader | 252/173 |
| 4,387,090 | 6/1983 | Bolich, Jr. | 424/70 |
| 4,397,836 | 8/1983 | Madrange et al. | 424/47 |
| 4,450,152 | 5/1984 | Ona et al. | 424/70 |
| 4,472,375 | 9/1984 | Bolich, Jr. et al. | 424/70 |
| 4,487,883 | 12/1984 | Homan | 524/792 |
| 4,502,889 | 3/1985 | Kurita | 106/287.12 |
| 4,515,784 | 5/1985 | Bogardus et al. | 514/63 |
| 4,529,586 | 7/1985 | DeMarco et al. | 424/70 |
| 4,559,227 | 12/1985 | Chandra et al. | 424/70 |
| 4,668,508 | 5/1987 | Grollier et al. | 424/70 |
| 4,704,272 | 11/1987 | Oh et al. | 424/70 |
| 4,728,457 | 3/1988 | Fieler et al. | 252/174.15 |
| 4,741,855 | 5/1988 | Grote et al. | 252/142 |
| 4,761,273 | 8/1988 | Grollier et al. | 424/47 |
| 4,764,363 | 8/1988 | Bolich, Jr. | 424/47 |
| 4,788,006 | 11/1988 | Bolich, Jr. et al. | 252/550 |
| 4,834,968 | 5/1989 | Bolich, Jr. | 424/70 |
| 4,840,786 | 6/1989 | Johnson et al. | 424/43 |
| 4,842,850 | 6/1989 | Vu | 424/70 |
| 4,871,529 | 10/1989 | Sramer | 424/47 |
| 4,902,499 | 2/1990 | Boush | 424/47 |

FOREIGN PATENT DOCUMENTS

| | | |
|---|---|---|
| 1222461 | 6/1987 | Canada . |
| 028853 | 5/1981 | European Pat. Off. . |
| 116207 | 8/1984 | European Pat. Off. . |
| 155806 | 9/1985 | European Pat. Off. . |
| 288012 | 10/1988 | European Pat. Off. . |
| 56-022716 | 3/1981 | Japan . |
| 56-129300 | 10/1981 | Japan . |
| 57-162768 | 10/1982 | Japan . |
| 58-177909 | 10/1983 | Japan . |
| 61-044972 | 3/1986 | Japan . |
| 61-158914 | 7/1986 | Japan . |
| 61-161214 | 7/1986 | Japan . |
| 61-195138 | 8/1986 | Japan . |
| 2170216A | 7/1986 | United Kingdom . |

OTHER PUBLICATIONS

Chemical Abstracts vol. 94, No. 2, May 1981, p. 373, Column 1, Abstract No. 162601q.
Chemical Abstracts, vol. 97, No. 23, Dec. 1982, p. 324, column 1, Abstract No. 203098p.
U.S. Ser. No. 031,480, Bolich, Jr. et al., filed Mar. 27, 1987.
U.S. Ser. No. 112,975, Cobb et al., filed Oct. 23, 1987.
U.S. Ser. No. 429,895, Murphy et al., filed Oct. 31, 1989.
U.S. Ser. No. 427,213, Maksimoski et al., filed Oct. 31, 1989.

Primary Examiner—Merrell C. Cashion, Jr.
Assistant Examiner—P. L. Prater
Attorney, Agent, or Firm—Gretchen R. Hatfield; Steven J. Goldstein

[57] ABSTRACT

Silicone hairspray compositions which give hair volume and hold but with a soft feel are disclosed. These compositions comprise from about 0.05% to about 10.0% of a nonrigid silicone gum, said gum having dispersed therein from about 0.03% to about 8.0% of unsolubilized particulate matter which is preferably an octyl acrylamide/acrylate/butyl aminoethyl methacrylate copolymer; from about 0.05% to about 5.0% of a hydrophobically-modified clay suspending/anti-agglomerating agent; and a volatile carrier, such as ethanol.

24 Claims, No Drawings

SILICONE HAIRSPRAY COMPOSITIONS

TECHNICAL FIELD

The present invention relates to silicone-containing hairspray compositions which provide improved hair conditioning and style retention properties due to the inclusion of silicone gums having dispersed therein unsolubilized particulate matter. Agglomeration of the silicone gum is prevented by inclusion in the composition of a hydrophobically-modified clay which acts as a suspending/anti-agglomerating agent.

BACKGROUND OF THE INVENTION

The desire to have hair retain a particular shape is widely held. The two methodologies of accomplishing this are permanent chemical alteration of the hair or temporary alteration. A temporary alteration is one which can be removed by water or by shampooing. This has generally been accomplished by means of the application of a composition to dampened hair after shampooing and/or conditioning or to dry styled hair. The materials used to provide setting benefits have generally been resins or gums and have been applied in the form of mousses, gels, lotions, or sprays. Many people desire a high level of style retention such as that provided by a typical hair-spray composition without the negative impact that these materials generally have on dry hair properties, particularly hair manageability and hair feel.

Silicones in various hair care compositions have been disclosed in a large number of different publications, including U.S. Pat. No. 3,964,500, Drakoff, issued June 22, 1976; U.S. Pat. No. 4,364,837, Pader, issued Dec. 21, 1981; U.S. Pat. No. 4,341,799, Good, issued July 27, 1982; U.S. Pat. No. 4,465,619, Boskamp, issued Aug. 14, 1984; U.S. Pat. No. 4,515,784, Bogartus, issued May 7, 1985; U.S. Pat. No. 4,387,090, Bolich, issued June 7, 1983; and U.S. Pat. No. 4,529,586, DeMarco et al., issued July 16, 1985.

Silicone fluids in aqueous-based hair mousse compositions are disclosed in U.S. Pat. No. 4,764,363, Bolich, Jr., issued Aug. 16, 1988. Silicone gums in aqueous-based hair mousse compositions are disclosed in U.S. Pat. No. 4,834,968, Bolich, Jr. et al., issued May 30, 1989.

Hair care compositions containing hair styling polymers such as an octylacrylamide/acrylate/butylaminoethyl methacrylate copolymer have also been disclosed. Canadian Patent No. 1,222,461. Varco, issued June 2, 1987, and U.S. Pat. No. 4,397,836, Mandrange et al., issued Aug. 9, 1983, disclose hair spray compositions comprising such copolymers solubilized in alcohol. Delivery of the copolymer to hair in this form (i.e., solubilized) provides style hold benefits but leaves the hair feeling stiff and sticky. The aerosol mousse compositions disclosed in U.S. Pat. No. 4,764,363, Bolich, Jr., issued Aug. 16, 1988, may also optionally comprise a hair setting polymer which may be the above-named copolymer. The polymer is again solubilized in the composition.

Ser. No. 274,218, Maksimoski and Murphy, filed Nov. 21, 1988, discloses hair care compositions comprising certain silicone gums having dispersed therein certain particulate materials, which are not solubilized in the composition, to provide increased hair volume benefits and style retention. The compositions provide these benefits to the hair without negatively affecting dry hair properties such as ease of combing.

This is surprising since other silicone materials which have been typically used in hair care compositions as conditioners have decreased perceived hair volume and hurt style retention, and the resins and gums used frequently for style retention have generally hurt dry hair properties such as combing. Furthermore, the hair styling polymers such as an octylacrylamide/acrylate/butylaminoethyl methacrylate copolymer, as traditionally used in hair styling compositions (i.e., solubilized therein), leave hair feeling stiff and sticky.

Though silicone gums have traditionally been difficult to formulate in typical hair spray compositions, comprising, e.g., an ethanol solvent, a method has now been discovered to make such formulations possible. This method comprises using a hydrophobically-modified clay as a dispersing/anti-agglomerating agent for the silicone gum.

Such materials have been used in the past as suspending agents for personal care compositions containing particulate materials. For example, EPO patent application No. 0028853, Beckmeyer et al., published May 20, 1981, discloses antiperspirant compositions comprising particulate antiperspirant salts, silicone fluids, and bulking/suspending agents which may be hydrophobically-modified clays. See also. U.S. Pat. No. 4,840,786, Johnson et al, issued June 20, 1989. U.S. Pat. No. 4,152,416, Spitzer et al., issued May 1979, discloses antiperspirant compositions comprising antiperspirant salts, silicone gums, and bulking agents which may be colloidal silica or hydrophobic clays.

It is an object of the present invention to formulate hair spray compositions which provide a look of increased hair volume.

It is also an object of the present invention to formulate hair spray compositions which provide good style retention.

It is a further object of the present invention to formulate hair spray compositions containing silicone gums which provide good hair conditioning, and leave hair feeling soft.

These and other objects will become readily apparent from the detailed description which follows.

Unless otherwise indicated, all percentages and ratios herein are by weight.

SUMMARY OF THE INVENTION

The present invention relates to hair spray compositions comprising from about 0.05% to about 10% of a nonrigid silicone gum having a viscosity of from about 1,000,000 centistoke to about 20,000,000 centistoke; said gum having dispersed therein from about 0.01% to about 8%, by weight of the composition, of unsolubilized particulate matter selected from a group of materials which will not interact with the silicone gum; from about 0.05% to about 5.0% of a hydrophobically-modified clay suspending/anti-agglomerating agent; and a volatile carrier.

DETAILED DESCRIPTION OF THE INVENTION

The essential as well as optional components are described below.

Silicone Gum

The compositions of the present invention contain, as an essential component, a nonrigid silicone gum which when applied to hair imparts style retention and conditioning benefits.

By a nonrigid gum is meant a thick, viscous, amorphous fluid polymer where, above its glass transition temperature, it can be considered a processable, ductible flow. Ideally, this flow should be slow enough to give it the outward appearance of a solid.

The nonrigid silicone gums useful in the present invention have complex viscosities of at least about 100,000 centistoke (CSTK) and up to about 300,000,000 CSTK and, preferably from about 1,000,000 CSTK to about 20,000,000 CSTK, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

Nonrigid silicone gums useful in the present invention include, but are not limited to, polydimethyl siloxane gums including those having end groups such as hydroxyl, cross-linked siloxanes such as organic substituted silicone elastomers, organic substituted siloxane gums including those having end groups such as hydroxyl, resin reinforced siloxanes and cross linked siloxane polymers.

The preferred nonrigid silicone gum of the present invention is polydimethyl siloxane gum having a viscosity of from about 1,000,000 CSTK to about 20,000,000 CSTK. An additional nonrigid silicone gum useful in the invention is a diphenyl-dimethyl polysiloxane gum having a molecular weight of at least about 500,000, which is diphenyl substituted to the extent of 3% or more, preferably at least about 5%, and having a viscosity of about 10,000,000 CSTK.

The gum comprises from about 0.05% to about 10%, preferably from about 0.05% to about 7%, of the hair spray composition.

Non-solubilized Particulate

The present invention further comprises, as a second essential component, unsolubilized inert particulate matter. This particulate must be dispersed in the silicone gum, not solubilized in the hair spray solvent. Keeping the particulate unsolubilized and dispersed in the silicone gum is believed to be the key to providing the unique hair volumizing benefit of the hair spray compositions of this invention.

The particulate matter remains as a particulate dispersed in the gum even after the gum is mixed into a fully formulated hair spray composition. When the composition is applied to hair it is believed that the silicone gum containing the particulate is deposited onto and coats the individual hair shafts. The silicone gum provides well-known hair style retention and conditioning benefits. The particulate matter prevents overconditioning of the hair by the silicone gum. This results in a hairspray composition which provides hair conditioning and hair manageability with a softer feeling hair hold.

The particulate matter may be any non-water-soluble particulate material capable of being dispersed in the silicone gum which does not interact with the silicone gum in any way, e.g., through chemical reaction or bonding. That is, the particulate remains an inert dispersion in the silicone gum.

Preferably the particulate matter dispersed in the gum is of an average particle size of from about $0.1\mu$ to about $15\mu$, most preferably from about $0.15\mu$ to about $2.0\mu$. The particle size of the particulate matter to be dispersed into the gum may be larger than this since during the process of combining the particulate with the gum the particles may be broken down into the smaller desired particle size. Particles of this size are small enough to be easily dispersed in the gum and unnoticeable on hair but large enough to provide an increased hair volume benefit, i.e., large enough to allow for separation of the hair shafts when deposited there-between and thereon.

Any particulate material which meets the above outlined criteria may be used in the present invention. Non-limiting examples of useful particulate materials include particulate polymeric film forming/hair styling materials such as aluminum starch octenyl-succinate, sold under the tradename Dry Flo ® (available from the National Starch Company); acrylate/acrylamide copolymer sold under the tradename Ultra Hold 8 ® (available from BASF Corp.); polyvinyl methyl ether/maleic anhydride copolymer powder sold under the tradename Gantrez AN ® (available from GAF Corp.); vinyl acetate/crotonic acid copolymer sold under the tradename Luviset CA-66 ® (available from BASF Corp.). Non-polymeric particulate matter will also work in the present invention, again, as long as the material meets the requirements outlined above. Non-limiting examples of such materials are titanium dioxide, calcium carbonate and talc.

The particulate matter is included in the hair spray compositions of the present invention at a level of from about 0.01% to about 8.0%, preferably from about 0.01% to about 5.0%, by weight of the total composition.

The particulate is dispersed in the silicone gum via any conventional mixing means that will homogeneously disperse the particulate in the gum prior to mixing the gum with other components of the hair care compositions.

The preferred particulate material of the present invention is an octyl acrylamide/acrylate/butylaminoethyl methacrylate copolymer particulate. This material is present in the hair spray compositions of this invention at a level of from about 0.01% to about 0.5%. This material is dispersed in the silicone gum prior to combining with any other components in the hair spray compositions of the present invention, and remains unsolubilized in the final fully formulated compositions. The average particle size of this material in the gum should be from about $0.15\mu$ to about $2.0\mu$.

The compositions of the invention preferably comprise a volatile silicone solvent, or mixtures thereof, for the gum. The silicone solvent, if present, is at a level of from about 0.01% to about 10%, preferably from about 0.05% to about 5.0%, of the composition. The silicone solvent allows for preservation of the dispersion of the particulate in the silicone gum while the viscosity of the gum is lowered so that it can be incorporated into the hair spray composition. The term "volatile" as used herein means that the material has a measurable vapor pressure.

The preferred volatile silicone solvents have a boiling point between about 99° C. and about 260° C. and have a solubility in water of less than about 0.1%. The degree of substitution on the siloxane (higher substitution, lower solubility) obviously affects the polymer's solubility and must be taken into account by the formulator. The silicones may be either cyclic or linear polydimethyl siloxanes. The number of silicon atoms in the cyclic silicones is about 3 to about 7, most preferably 4 or 5. The general formula for the cyclic silicones is:

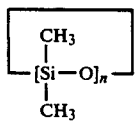

wherein n=3-7. Viscosities are generally less than about 10 centipoise (cP) at 25° C.

Linear polydimethyl siloxanes useful in the present invention generally have viscosities of less than about 5 cP at 25° C. The linear volatile silicones contain from about 3 to about 9 silicone atoms and have the general formula:

(CH$_3$)$_3$Si—O—[Si(CH$_3$)$_2$O]$_n$Si(CH$_3$)$_3$ wherein n=1-7.

Silicones of the above-described types are widely available e.g., from Dow Corning as 344, 345 and 200 fluids; Union Carbide as Silicone 7202 and 7158; and Stauffer Chemical as SWS-03314.

The preferred volatile silicone solvent of the present invention is cyclomethicone available from G. E. Silicones. It is present in the compositions of the present invention at from about 0.05% to about 5.0%.

The volatile silicone solvent is preferably combined with the silicone gum/particulate matter in several steps to further assure preservation of the dispersion. Any conventional means for mixing the two may be utilized.

An optional component of the present invention is a silicone resin. Incorporation of the silicone resin into the compositions of the present invention is believed to increase the adherence of the silicone gum/particulate matter to the hair.

Silicone resins are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. The silicone resin is present in the compositions of the present invention at from about 0.01% to about 10%. A preferred resin is one offered by General Electric as GE SR545. This resin is preferably solubilized in the volatile carrier component, e.g., cyclomethicone, before combination with other hair care composition components, or the silicone gum/particulate matter.

Hydrophobically-treated Clay

The hairspray compositions of this invention contain as a critical component hydrophobically-treated or hydrophobically-modified clays as suspending/anti-agglomerating agents. Use of these particular materials in the present compositions allows for the formulation of a silicone hairspray product which was previously impossible. Though silicone gum can be finely dispersed in hairspray solvents such as ethanol, it tends to precipitate out of solution over time and form a solid mass at the bottom of the container. This solid mass is un-redispersible in the ethanol upon agitation. Though hair spray compositions formulated with these clay materials will still separate into two phases (a volatile carrier phase and a silicone gum phase) over time, the presence of the clay materials allows for redispersion of the silicone gum in the volatile carrier with a gentle shake of the container.

The suspending/anti-agglomerating agents useful herein include hydrophobically-treated montmorillonite clays, e.g., bentonites and hectorites. Untreated clays will not provide the same suspending/anti-agglomerating benefits in the present invention. The hectorite and bentonite hydrophobically-treated clay minerals of the instant compositions can be described as expandable (swellable), three-layer clays, in which a sheet of aluminum/oxygen atoms or magnesium/oxygen atoms lies between two layers of silicone/oxygen atoms, i.e., aluminosilicates and magnesium silicates, having an ion exchange capacity of at least about 50 meq/100 g of clay, and preferably at least about 60 meq/100 g of clay. The term "expandable" as used to describe clays relates to the ability of the layered clay structure to be swollen or expanded on contact with water. Such hectorite and bentonite clays are described in Grim, *Clay Mineralogy* (2nd. Ed.) pp. 77–79 (1968), and in Van Olphen, *An Introduction to Clay Colloid Chemistry*, (2nd Ed.) pp 64–76 (1977), both of which are incorporated by reference herein.

The clay minerals employed in the compositions of the instant invention contain exchangeable cations including, but not limited to, protons, sodium ions, potassium ions, calcium ions, magnesium ions, lithium ions, and the like.

It is customary to distinguish between clays on the basis of one cation predominantly or exclusively absorbed. For example, a sodium clay is one in which the absorbed cation is predominantly sodium. As used herein, the term clay, such as a hectorite clay, includes all the various exchangeable cation variants of that clay, e.g., sodium hectorite, potassium hectorite, lithium hectorite, magnesium hectorite, calcium hectorite, etc.

The clay minerals employed in the compositions of the instant invention are made hydrophobic by treating them with a cationic surfactant material. A preferred cationic surfactant is a quaternary ammonium cationic surfactant. A particularly preferred cationic surfactant is ditallow dimethyl ammonium chloride (e.g., quaternium-18).

Several of these hydrophobically-treated clay agents are commercially available. They include, for example, quaternium-18-bentonite, sold under the tradenames Bentone-34 ® by NL chemical and Tixogel VP ® by United Catalysts; quaternium-18-hectorite, sold under the tradename Bentone-38 ® by NL Chemicals; stearalkonium bentonite, sold under the tradename Tixogel-VZ ® by United Catalysts; and stearalkonium hectorite, sold under the trade name Bentone-27 ® by NL Chemicals.

The hydrophobically-modified clay is present in the hairspray compositions of the present invention at a level of from about 0.05% to about 5.0%, preferably from about 0.05% to about 2.0%, by weight of the hairspray composition.

A small amount of water is required in the hairspray compositions of the present invention to activate the clay agent. Generally this requirement can be met by using a 190-proof ethanol solvent for the system. Alternatively, a small amount of water can be added to the hair spray composition.

An additional dispersing aid may be added to the hairspray compositions of the present invention to make redispersion of the silicone gum after phase separation easier. Dimethicone copolyol is a preferred dispersing aid. It may be added to the present hairspray compositions at a level of from about 0.01% to about 5%.

Volatile Carrier

The present hairspray compositions also comprise a volatile carrier system. This can comprise any of those conventionally used in resin hairspray formulations, preferably a $C_1-C_6$ alkanol, most preferably ethanol. This component "carries" the silicone gum to the hair then volatilizes, leaving the particulate containing gum behind on the hair to provide hair conditioning, hair volumizing benefits, and hairstyling hold. The carrier is present in the hairspray composition at from about 20% to about 95%, preferably from about 35% to about 95%, by weight of the composition. Water can also be used to substitute for part of the volatile carrier component.

Hair Hold Resin

An additional component, that is preferably used in the present hairspray compositions, is a hair setting polymer. Any polymer soluble or dispersible in the volatile carrier or solvent phase may be used. Solubility/dispersibility is determined at ambient conditions (e.g., temperature about 25° C. and atmospheric pressure). Suitable types of polymers include anionic, non-ionic, amphoteric and cationic polymer materials. Specific polymers include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether-maleic acid), and octylacrylamide/acrylate/-butylaminoethyl methacrylate copolymers. Mixtures of polymers may also be used. PVP and PVP copolymers with other monomers are preferred. The most preferred resins for use in the present hairsprays are copolymers of polyvinyl pyrrolidone and vinyl acetate.

These hair hold resins can be the same materials as those used as the particulate material dispersed in the silicone gum of the present invention. Though the material may be the same, it is providing two separate functions in the present compositions. When it is dispersed as a particulate in the gum, it prevents over conditioning of the hair by the silicone gum and may provide hair volumizing benefits to the composition, as discussed supra. When the hair-hold or hair-setting polymer is solubilized in the volatile carrier or solvent it is providing a traditional style-holding benefit to the present hair spray compositions. Though the silicone gum (having the particulate dispersed therein) provides soft hair feel, increased hair manageability, and increased hair volume benefits, it does not, itself, provide significant hair hold, hence, the potential need for a separate hair style/hold agent. These various components provide the user of the present compositions with a hairspray which after application provides hair styling hold, but with a softer feel to hair than traditional hair spray products provide.

With certain of the polymers it may be necessary to neutralize some acidic groups to promote solubility/dispersibility (e.g., PVA/crotonic acid). Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS).

When present the polymer(s) is used at a level of from about 0.25% to about 20%, preferably from about 1% to about 20%, of the total composition. The mass average molecular weight of the polymer is not critical, but is generally in the range of from about 2,000 to about 2,000,000.

Propellant

The present hairspray compositions may be formulated in aerosol or non-aerosol forms. If an aerosol hairspray is desired, a propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than 1 so that pure propellant is not emitted from the container. Examples of materials that are suitable for use as propellants are trichlorofluoromethane, dichlorodifluoromethane, dichlorotetrafluoroethane, monochlorodifluoromethane, trichlorotrifluoroethane, dimethylether, propane, n-butane and isobutane, used singly or admixed. The hydrocarbons, particularly isobutane, used singly or admixed with other hydrocarbons are preferred due to their densities being less than 1.

The amount of the propellant gas is governed by normal factors well known in the aerosol art. For hairsprays the level of propellant is generally from about 3% to about 30%, preferably from about 5% to about 15%, of the total composition. If a propellant such as dimethylether utilizes a vapor pressure suppressant (e.g., trichloroethane or dichloromethane) the amount of suppressant is included as part of the propellant.

The hair spray compositions herein can contain other optional components suitable for rendering such compositions more acceptable. Such conventional optional ingredients are well known to those skilled in the art and include such things as fragrances, sunscreens and proteins. As with all compositions, the present compositions should not contain components which unduly interfere with the performance of the compositions.

The pH of the present compositions is between about 3 and about 7, preferably between about 4 and about 6. Keeping the pH on the acidic side prevents solubilization of the particulate out of the gum and into the volatile solvent.

METHOD OF MAKING

The hair spray compositions of the present invention can be made using any conventional formulations and mixing techniques. However, it is critical that the particulate matter be dispersed in the silicone gum prior to combination with the other hair spray composition components. If a volatile silicone carrier is used in the compositions of the present invention to lower the viscosity of the silicone gum, it is preferably combined with the silicone gum in several steps. Mixing the volatile carrier and silicone gum together this way avoids disruption of the homogeneous dispersion of the particulate matter in the gum. If a silicone resin is also used in the composition, it should preferably be mixed with the volatile carrier prior to combination of the carrier material with the gum.

Methods of making hair spray compositions of the present invention are described more specifically in the following examples.

METHOD OF USE

The hair spray compositions of the present invention are used in conventional ways to provide the hair conditioning/styling/holding benefits of the present invention. Such method generally involves application of an effective amount of the product to dry and/or slightly damp hair before and/or after the hair is styled. By "effective amount" is meant an amount sufficient to provide the hair conditioning volume and style benefits desired considering the length and texture of the hair. Use of the compositions of the present invention in this manner provides hair conditioning, hair holding and volumizing benefits, while at the same time leaving the hair with a softer feel and more manageability than traditional hairspray products provide.

The following Examples further illustrate the preferred embodiments within the scope of the present invention. The Examples are given solely for the purposes of illustration and are not to be construed as limitations of the present invention as many variations of the invention are possible without departing from its spirit and scope.

EXAMPLE I

| EXAMPLE I Non-Aerosol Silicone Hairspray | |
|---|---|
| Component | Weight % |
| Ethanol (190 proof) | 87.439 |
| PVP/VA copolymer (50/50) | 10.00 |
| Cyclomethicone[1] | 1.60 |
| Dimethicone copolyol[2] | 0.50 |
| Amphomer[3] particulate | 0.05 |
| Tixogel VP[4] | 0.10 |
| Polydimethylsiloxane gum[5] | 0.20 |
| Octyl Salicylate | 0.01 |
| Keratin Amino Acids | 0.001 |
| Fragrance | 0.10 |
| | 100% |

[1]Cyclomethicone having a D5 structure available from GE Silicones
[2]FF400 Dimethicone Copolyol available from Dow Corning
[3]Octylacrylamide/Acrylate/Butyl Aminoethyl Methacrylate Copolymer having an original particle size (before milling) of 75–200 microns, available from National Starch
[4]Quaternium 18-Bentonite available from United Catalysts
[5]SE-30 Gum available from GE Silicones The Amphomer ® particulate is first dispersed in the polydimethyl siloxane gum using a dough style mixer at low speed for about 4 hours. The Amphomer ® gum mixture is then added to the cyclomethicone and mixed until dissolved using a dough style mixer for about 8 hours. The dimethicone copolyol is added and the composition mixed using the dough style mixer until homogeneous. The Tixogel ® is then added and mixed using the dough style mixer until homogeneous. Using a Tek Mar ® mill the composition is slowly milled with the ethanol until homogeneous. Using conventional mixing the PVP/VA copolymer is added. The octyl salicylate, keratin amino acids, and fragrance are mixed into the composition in that order.

The hairspray composition should be shaken well before each use to redisperse the silicone gum.

The resulting hairspray provides improved hair conditioning and volumizing benefits with a softer feeling hair hold.

Substantially similar results are obtained when an equivalent amount of a quaternium-18-hectorite (for example, the material sold under the tradename Bentone-38 ® by NL Chemicals); a stearalkonium bentonite (for example, the material sold under the trade name Tixogel VZ ® by United Catalysts) or a stearalkonium hectorite (for example, the material sold under the tradename Bentone-27 ® by NL Chemicals), is substituted for the Tixogel VP ® clay.

EXAMPLE II

An aerosol silicone hairspray can be prepared by combining the composition of Example I with a propellant, for example, A-31 propellant, which is an isobutane propellant, available from Phillips Petroleum Company, at a ratio of 3 parts hairspray composition to 1 part propellant.

What is claimed is:

1. A hair spray composition comprising:
    (a) from about 0.05% to about 10.0% by weight of the composition, of a non-rigid silicone gum having a viscosity of from about 100,000 centistoke to about 300,000,000 centistoke, said gum having dispersed therein from about 0.01% to about 8.0%, by weight of the composition, of unsolubilized particulate matter which will not interact with the silicone gum;
    (b) from about 0.05% to about 5.0% by weight of the composition of a hydrophobically-modified quatermary ammonium treated montmorillonite clay agent or mixtures thereof; and
    (c) from about 20% to about 95% of a volatile carrier.

2. The composition of claim 1 wherein the nonrigid silicone gum comprises from about 0.05% to about 7.0% of the composition and the unsolubilized particular matter comprises from about 0.01% to about 5.0% of the composition.

3. The composition of claim 2 wherein the viscosity of the nonrigid silicone gum is from about 1,000,000 centistoke to about 20,000,000 centistoke.

4. The composition of claim 3 wherein the unsolubilized particulate matter is selected from the group consisting of octyl acrylamide/acrylate/butylaminoethyl methacrylate copolymer; aluminum starch octenyl succinate; polyvinyl methyl ether maleic anhydride copolymer; acrylate/acrylamide copolymer; vinyl acetate/crotonic acid copolymer; titanium dioxide; calcium carbonate; talc and mixtures thereof.

5. The composition of the claim 4 wherein the unsolubilized particular matter has an average particle size of from about $0.1\mu$ to about $15.0\mu$.

6. The composition of claim 5 wherein the nonrigid silicone gum is polydimethyl siloxane gum having a viscosity of from about 1,000,000 centistoke to about 20,000,000 centistoke.

7. The composition of claim 6 having a pH of from about 3 to about 7.

8. The composition of claim 7 wherein the unsolubilized particulate matter is an octylacrylamide/acrylate/butylaminoethyl methacrylate copolymer having a particle size of from about $0.15\mu$ to about $2.0\mu$.

9. The composition of claim 8 which additionally comprises from about 0.01% to about 10% of a volatile silicone solvent for the silicone gum.

10. The composition of claim 9 wherein the volatile silicone solvent is a cyclic silicone containing from about 3 to about 7 silicon atoms.

11. The composition of claim 10 wherein the volatile silicone solvent is cyclomethicone and is present at a level of from about 0.05% to about 5.0% of the composition.

12. A hair care composition according to claim 11 wherein the nonrigid silicone gum is a polydimethyl siloxane gum having a viscosity of from about 1,000,000 centistoke to about 20,000,000 centistoke and the unsolubilized particulate material is an octylacrylamide/acrylate/butylaminoethyl methacrylate copolymer having a particle size of from about $0.15\mu$ to about $2.0\mu$.

13. A hair care composition according to claim 1 wherein the nonrigid silicone gum is a polydimethyl siloxane gum having a viscosity of from about 1,000,000 centistoke to about 20,000,000 centistoke and the unsolubilized particulate material is an octylacrylamide/acrylate/butylaminoethyl methacrylate copolymer having a particle size of from about $0.15\mu$ to about $2.0\mu$.

14. The composition of claim 1 wherein the hydrophobically-modified clay agent comprises from about 0.05% to about 2.0% of the composition.

15. The composition of claim 14 wherein the hydrophobically-modified clay agent is selected from the group consisting of hydrophobically-modified hectorite, hydrophobically-modified bentonite and mixtures thereof.

16. The composition of claim 15 wherein the hydrophobically-modified clay agent is selected from the group consisting of quaternium-18-bentonite, quaternium-18-hectorite, stearalkonium bentonite, stearalkonium hectorite, and mixtures thereof.

17. The composition of claim 1 wherein the volatile carrier is selected from the group consisting of $C_1$–$C_6$ alkanols.

18. The composition of claim 17 wherein the volatile carrier is ethanol.

19. The composition of claim 1 additionally comprising from about 0.25% to about 20% of a hair-holding resin selected from the group consisting of poly vinyl/pyrrolidone, copolymers of poly vinyl pyrrolidone and methylmethacrylate, copolymers of poly vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methacrylic acid terpolymer, vinyl acetate/crotonic acid/vinyl neodecanoate copolymer, octyl acrylamide/acrylates copolymer, monoethyl ester of poly (methyl vinyl ether maleic acid), octyl acrylamide/acrylate/butylaminoethyl methacrylate copolymers and mixtures thereof; which is solubilized in the volatile carrier.

20. The composition of claim 19 wherein the hair holding resin comprises from about 1% to about 20% of a copolymer of polyvinyl pyrrolidone and vinyl acetate.

21. The composition of claim in aerosol form additionally comprising from about 3% to about 30% of a propellant.

22. The composition of claim 21 wherein the propellant is selected from the group consisting of trichlorofluoromethane, dichlorodifluoromethane, dichlorotetrafluoroethane, monochlorodifluoromethane, trichlorotrifluoroethane, dimethylether, propane, n-butane, isobutane and mixtures thereof.

23. A hairspray composition comprising:
  (a) from about 0.05% to about 7.0% by weight of the composition, of a non-rigid polydimethyl siloxane gum having a viscosity of from about 1,000,000 centistoke to about 20,000,000 centistoke, said gum having dispersed therein from about 0.01% to about 5.0%, by weight of the composition, of unsolubilized octylacrylamide/acrylate/butyl aminoethyl methacrylate copolymer particulate matter having an average particle size of from about $0.15\mu$ to about $2.0\mu$;
  (b) from about 0.05% to about 5.0%, by weight of the composition, of a volatile silicone solvent for the polydimethyl siloxane gum;
  (c) from about 0.05% to about 2.0% by weight of the composition of a hydrophobically modified clay agent selected from the group consisting of a quaternium-18-bentonite, quaternium-18-hectorite, stearalkonium bentonite, stearalkonium hectorite, and mixtures thereof;
  (d) from about 1% to about 20% of a hair-holding resin which is selected from the group consisting of poly vinyl/pyrrolidone, copolymers of poly vinyl pyrrolidone and methylmethacrylate, copolymers of poly vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methacrylic acid terpolymer, vinyl acetate/crotonic acid/vinyl neodecanoate copolymer, octylacrylamide/acrylates copolymer, monoethyl ester of poly (methyl vinyl ether maleic acid), octyl acrylamide/acrylate/butylaminoethyl methacrylate copolymers and mixtures thereof; which is solubilized in the volatile carrier; and
  (e) from about 35% to about 95% of ethanol.

24. A process for making the hair care composition of claim 1 comprising mixing the particulate matter and the silicone gum until the particulate matter is homogeneously dispersed in the gum and has a particle size of from about $0.15\mu$ to about $2\mu$, mixing the gum/particulate mixture with the hydrophobically-modified clay; and dispersing this composition in the volatile carrier.

* * * * *